(12) United States Patent
MacDonald, II et al.

(10) Patent No.: US 9,938,170 B2
(45) Date of Patent: *Apr. 10, 2018

(54) SYNTHETIC ACID AND ASSOCIATED METHODS

(71) Applicant: Green Products & Technologies, L.L.C., Melbourne, FL (US)

(72) Inventors: John T. MacDonald, II, Grant, FL (US); John Thomas MacDonald, III, West Melbourne, FL (US)

(73) Assignee: Green Products & Technologies, L.L.C., Melbourne, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/613,678

(22) Filed: Jun. 5, 2017

(65) Prior Publication Data

US 2017/0334754 A1 Nov. 23, 2017

Related U.S. Application Data

(60) Continuation of application No. 15/131,364, filed on Apr. 18, 2016, now Pat. No. 9,670,079, which is a continuation of application No. 14/739,227, filed on Jun. 15, 2015, now Pat. No. 9,315,400, which is a continuation of application No. 14/471,055, filed on Aug. 28, 2014, now Pat. No. 9,056,815, which is a division of application No. 13/110,330, filed on May 18, 2011, now Pat. No. 8,853,446.

(60) Provisional application No. 61/417,948, filed on Nov. 30, 2010.

(51) Int. Cl.

| C07C 229/00 | (2006.01) |
|---|---|
| C02F 1/00 | (2006.01) |
| B01F 5/00 | (2006.01) |
| C02F 1/66 | (2006.01) |
| B01F 5/04 | (2006.01) |
| B01F 5/06 | (2006.01) |
| C07C 229/08 | (2006.01) |
| C09K 8/68 | (2006.01) |
| C09K 8/72 | (2006.01) |
| C11D 7/08 | (2006.01) |
| C11D 7/32 | (2006.01) |
| B01F 17/00 | (2006.01) |
| C09K 8/035 | (2006.01) |
| C09K 8/62 | (2006.01) |
| C09K 13/06 | (2006.01) |
| C02F 1/68 | (2006.01) |
| C02F 101/10 | (2006.01) |

(52) U.S. Cl.
CPC ............... *C02F 1/66* (2013.01); *B01F 5/043* (2013.01); *B01F 5/0415* (2013.01); *B01F 5/0609* (2013.01); *B01F 17/0042* (2013.01); *C02F 1/68* (2013.01); *C07C 229/08* (2013.01); *C09K 8/035* (2013.01); *C09K 8/62* (2013.01); *C09K 8/68* (2013.01); *C09K 8/72* (2013.01); *C09K 13/06* (2013.01); *C11D 7/08* (2013.01); *C11D 7/3245* (2013.01); *C02F 2101/10* (2013.01); *C02F 2305/00* (2013.01); *C09K 2208/26* (2013.01)

(58) Field of Classification Search
CPC .. C07C 229/08; C02F 1/66; C02F 1/68; B01F 229/08; C09K 8/00
USPC ...................................................... 562/553
See application file for complete search history.

(56) References Cited

U.S. PATENT DOCUMENTS

| 4,988,789 A | 1/1991 | Linder |
| 6,316,421 B1 | 11/2001 | Nantz et al. |
| 6,875,890 B1 | 4/2005 | Zhang |
| 2005/0256300 A1 | 11/2005 | Garetz et al. |

FOREIGN PATENT DOCUMENTS

JP 61243050 10/1986

OTHER PUBLICATIONS

H. Ashassi-Sorkhabi, M.R. Majidi, K. Seyyedi; "Investigation of Inhibition Effect of Some Amino Acids Against Steel Corrosion in HCI Solution;" Applied Surface Science 225; pp. 176-185; 2004.
International Search Report dated Jun. 12, 2012 for PCT/US11/62555.
Lian Yu et al.; "Glycine Crystallization During Spray Drying: The pH Effect on Salt and Polymorphic Forms"; Journal of Pharmaceutical Sciences, vol. 91, No. 11, pp. 2367-2375; Nov. 1, 2002.
Mohammed A. Amin, K.F. Khaled, Sahar A. Fadl-Allah; Testing Validity of the Tafel Extrapolation Method for Monitoring Corrosion of Cold Rolled Steel in HCI Solutions—Experimental and Theoretical Studies; Corrosion Science, 52 Pgs. 140-151; 2010.

*Primary Examiner* — Sikarl Witherspoon
(74) *Attorney, Agent, or Firm* — Stephen G. Anderson; GrayRobinson, P.A.

(57) ABSTRACT

Glycine is an organic compound that can be used in the making of a synthetic acid that obviates all the drawbacks of strong acids such as hydrochloric acid. The new compound is made by dissolving glycine in water, in a weight ratio of approximately 1:1 to 1:1.5. The solution is mixed until the glycine is essentially fully dissolved in the water Once dissolution is complete, hydrogen chloride gas is dissolved in the solution to produce the new compound, which can be referred to as hydrogen glycine. Also disclosed is a method for adjusting the pH of a fluid, the method comprising adding an effective amount of a solution to the fluid for adjusting the pH thereof to a desired level wherein the solution is prepared by mixing glycine in water to form a glycine solution; and adding hydrogen chloride to the glycine solution.

11 Claims, No Drawings

SYNTHETIC ACID AND ASSOCIATED METHODS

CROSS-REFERENCE TO RELATED APPLICATIONS

This application is a Continuation of, and claims priority to, U.S. patent application Ser. No. 15/131,364, filed Apr. 18, 2016, which itself is a Continuation of U.S. patent application Ser. No. 14/739,227, filed Jun. 15, 2015, now U.S. Pat. No. 9,315,400, which is a Continuation of U.S. patent application Ser. No. 14/471,055, filed Aug. 28, 2014, now U.S. Pat. No. 9,056,815, which itself is a Divisional of U.S. patent application Ser. No. 13/110,330, filed May 18, 2011, now U.S. Pat. No. 8,853,446, which itself claims priority to U.S. Provisional Application Ser. No. 61/417,948, filed Nov. 30, 2010, the disclosures of which are hereby incorporated by reference in their entirety and all commonly owned.

FIELD OF THE INVENTION

The present invention relates to compositions comprising synthetic acids and to methods of use for such compositions, including, but not limited to, removing cementitious materials from surfaces, hydraulic fracturing of oil and gas wells, adjusting the pH of well drilling fluids, adjusting the pH of process and waste waters, and solubilizing calcium carbonate in aqueous suspensions or dispersions thereof.

BACKGROUND

Acids by their very nature can be dangerous to use, handle, transport, and store. Further, most acids are not environmentally friendly.

Hydrochloric acid, for example, is a highly corrosive, strong acid that is used in many industrial and household applications including, but not limited to, surface cleaning and descaling operations, oil well acidification and hydraulic fracturing, and in the food industry. Concentrated hydrochloric acid is known to fume, forming an acidic mist that is corrosive and dangerous to both living tissue and metals.

Therefore, it would be beneficial to provide a synthetic acid that is safe to use for a plurality of applications and does not harm the environment or the user.

SUMMARY

The present invention is directed to a synthetic acid, method of making, and method of using. The acid comprises a glycine compound that is made by mixing glycine with hydrogen chloride gas.

The synthetic acid can be used in place of a plurality of known acids, oxidizers, and disinfectants, such as, but not intended to be limited to, hydrochloric, hydrofluoric, sulfuric, urea sulfuric, sulfamic, glycolic, acetic, phosphoric, nitric, formic, and citric acids, as well as urea hydrochloride, sodium hypochlorite, urea phosphate, formaldehyde, and quaternary ammonia.

Particular uses, also not intended as limitations, can include surface cleaning, concrete etching, hydraulic well fracturing, filter cake braking/cleaning, cementitious material removal, acidizing of wells, fruit and vegetable peeling, food preparation surface cleaning, turf and soil treatments, inert to herbicides and pesticides, agriculture and farm remediation, disinfecting, solubilizing calcium carbonate in aqueous suspensions and dispersions, treating waste water and industrial process water, and surface rust removal, and as a neutralizing agent to low pH acids.

It has further been discovered that this new compound can be considered organic, and can thus be deemed "organic" by the USDA. This will be of great benefit to all organic farmers and growers, whose current option for a low-pH soil mitigation or a low-pH inert is vinegar (glacial acidic acid), which in most cases is rendered useless for the intended application. Hydrogen glycine, being considered by the USDA as organic certified, is a viable alternative to the far-less-useful vinegar, as the pH of raw hydrogen glycine is −0.42, substantially exactly in line with that of hydrochloric or sulfuric acid.

Another benefit of the new compound is that it causes substantially no fuming during use, which is a great improvement over other known, traditional acids.

DETAILED DESCRIPTION OF EMBODIMENTS

A description of embodiments of the present invention will now be presented by way of example.

Glycine is an organic food grade compound having the formula $NH_2CH_2COOH$. Glycine is a crystalline solid that is known to be used commercially in pharmaceutical applications, as an agent in metal complexing and finishing, as an animal food additive, and in cosmetics.

The current applicant has found a new use for glycine, and that is in the making of a synthetic acid that obviates substantially all the drawbacks of strong acids such as hydrochloric acid.

The new compound is made by introducing glycine to water, for example, by way of an eductor jet pump, until the glycine is fully introduced into the water, in a weight ratio of approximately 1:1 to 1:1.5. For example, in a particular embodiment, when using a 10,000-gal batch reactor, 31,800 lbs. of glycine are dissolved into 32,600-48,600 lbs. of water. The solution is mixed, for example, with an inline static mixer until the glycine is essentially fully dissolved in the water.

Once dissolution is complete, hydrogen chloride gas is introduced, for example, with an inline eductor in the solution to produce the new compound, which will be referred to as hydrogen glycine. In the embodiment outlined above, 9500 liters of hydrogen chloride gas is introduced into the solution.

Although not intended as a limitation on the invention, applicant proposes that the following series of reactions creates the hydrogen glycine:

$$1NH_2CH_2COOH + 1H_2O \rightarrow 1NH_3^+CH_2COOH^- + 1H_2O \quad (1)$$

$$1NH_3^+CH_2COO^- + 1HCl \rightarrow 1Cl^-.NH_3^+CH_2COO^-.H^+ \quad (2)$$

Although the invention is not intended to be limited to the following explanation, it is theorized that in (1) the amine group deprotonates the carboxylic acid group to yield glycine zwitterions. In reaction (2), the hydrogen cation and chloride anion interact with the glycine. It may be that, owing to the differences in the dissociation constants of the carboxyl group and the amine group, the glycine ion has a stronger affinity for chloride than for hydrogen. The result is a solution with a minimal amount of free chloride ions and a pH typical of a strong acid, thus greatly reducing the corrosivity to near zero. The current composition has a corrosion level of 0.04 mmpy, well below the limit of 6.25 mmpy established in U.S. Federal DOT guidelines to receive a "non-corrosive" designation. Also, the glycine acts as a buffer, resisting changes to pH much more strongly than is known in traditional acids.

The composition of the present invention thus maintains its strength and pH much longer than is typical for strong acids. Thus less of the present composition is required for a given use as compared with previously known acids, thereby further reducing environmental impact as compared with known traditional strong acids.

It has been found that, not only does the inventive compound serve to replace more acidic and caustic substances, but hydrogen glycine has been found to "tame" strong acids interacting with substrates, thus reacting in such a manner as would a base, neutralizer, or an inhibitor. For example, when hydrogen chloride is placed on a metal such as aluminum or steel, a violent corrosive reaction takes place, thus gassing off (fuming) and corroding the metal surface. In addition, the fuming itself is corrosive. However, when hydrogen glycine is added to the hydrochloric acid on the metal surface, the reaction is substantially immediately tamed, and the corrosion and fuming stops. This same effect has been noted with other traditional acids such as sulfuric acid, phosphoric acid, urea hydrochloride, and glycolic acid. This corrosion inhibition can be effected in a wide range of concentrations, from 0.05% to 35% hydrogen glycine in acid.

Exemplary embodiments of the present disclosure include a method of making a synthetic acid comprising mixing glycine in water to form a glycine solution; and adding hydrogen chloride to the glycine solution. In one embodiment, the mixing comprises introducing the glycine into the water with the use of an eductor pump. In another embodiment, the adding comprises introducing the hydrogen chloride in gaseous form to the glycine solution. In yet another embodiment, the introducing comprises using an inline eductor.

The glycine may be mixed in the water in a weight ratio range of 1:1 to 1:1.5 glycine to water. Further, the mixing may be performed with the use of an inline static mixer. In one embodiment, the mixing continues until the glycine is essentially fully dissolved in the water. In another embodiment, the hydrogen chloride gas is added in a molar range of 1:1 to 2:1 glycine to hydrogen chloride.

Other methods in accordance with the embodiments disclosed herein include a method of assisting in hydraulic fracturing of an oil or gas well and adjusting the pH of well drilling fluids comprising adding to at least one of the well and the drilling fluid an effective amount of a solution of hydrogen glycine for adjusting the pH thereof to a desired level.

Also disclosed is a method of adjusting the pH of at least one of process and waste waters comprising adding to the at least one of the process and waste waters an effective amount of a solution of hydrogen glycine for adjusting the pH thereof to a desired level.

It is believed that the new compound has a multiplicity of benefits, not the least of which is that the elements are environmentally friendly, non-toxic, and non-corrosive, the ingredients being designated as FDA GRAS (generally regarded as safe). As discussed above, the new compound of the present invention can also replace or augment, and is safer to use than, traditional acids, and does not fume during use. Hydrogen glycine is also believed to be able to serve as a replacement for traditional sanitizers and disinfectants such as quaternary ammonia and sodium hypochlorite.

That which is claimed is:

1. A method for adjusting the pH of a fluid, the method comprising:
   mixing glycine with water to form a glycine solution;
   adding hydrogen chloride to the glycine solution to generate a solution; and
   adding an effective amount of the solution to the fluid for adjusting the pH thereof to a desired level.

2. The method of claim 1, wherein the fluid comprises a fluid associated with at least one of an oil well and a gas well.

3. The method of claim 1, wherein the fluid comprises at least one of an oil well and a gas well drilling fluid.

4. The method of claim 1, wherein the fluid comprises at least one of a process and a waste water.

5. The method of claim 1, wherein the mixing comprises introducing the glycine into the water with the use of an eductor pump.

6. The method of claim 1, wherein the adding comprises introducing the hydrogen chloride in gaseous form to the glycine solution.

7. The method of claim 6, wherein the introducing comprises using an inline eductor.

8. The method of claim 1, wherein the glycine is mixed with the water in a weight ratio range of about 1:1 to about 1:1.5 glycine to water.

9. The method of claim 1, wherein the mixing is performed with the use of an inline static mixer.

10. The method of claim 1, wherein the mixing continues until the glycine is essentially fully dissolved in the water.

11. The method of claim 1, wherein the hydrogen chloride is added in a molar range of about 1:1 to about 2:1 glycine to hydrogen chloride.

* * * * *